United States Patent [19]

Cook

[11] 4,042,626
[45] Aug. 16, 1977

[54] INTEGRATED TWO-STAGE UREA SYNTHESIS

[75] Inventor: Lucien H. Cook, Port Washington, N.Y.

[73] Assignee: Chemical Construction Corporation, New York, N.Y.

[21] Appl. No.: 271,072

[22] Filed: July 12, 1972

[51] Int. Cl.² ........................................... C07C 126/00
[52] U.S. Cl. .............................................. 260/555 A
[58] Field of Search ................................... 260/555 A

[56] References Cited

U.S. PATENT DOCUMENTS

| 3,046,307 | 7/1962 | Bochinski | 260/555 |
| 3,607,937 | 9/1971 | Otsuka | 260/555 |
| 3,607,938 | 9/1971 | Braun | 260/555 |

Primary Examiner—Bernard Helfin
Assistant Examiner—A. Siegel

[57] ABSTRACT

Urea synthesis in two stages, in which the first stage of ammonium carbamate formation is in indirect heat exchange with the second stage of ammonium carbamate dehydration to synthesize urea. Excess ammonia is separately preheated by heat exchange with the second stage and added to the main process stream between the first stage and the second stage.

7 Claims, 1 Drawing Figure

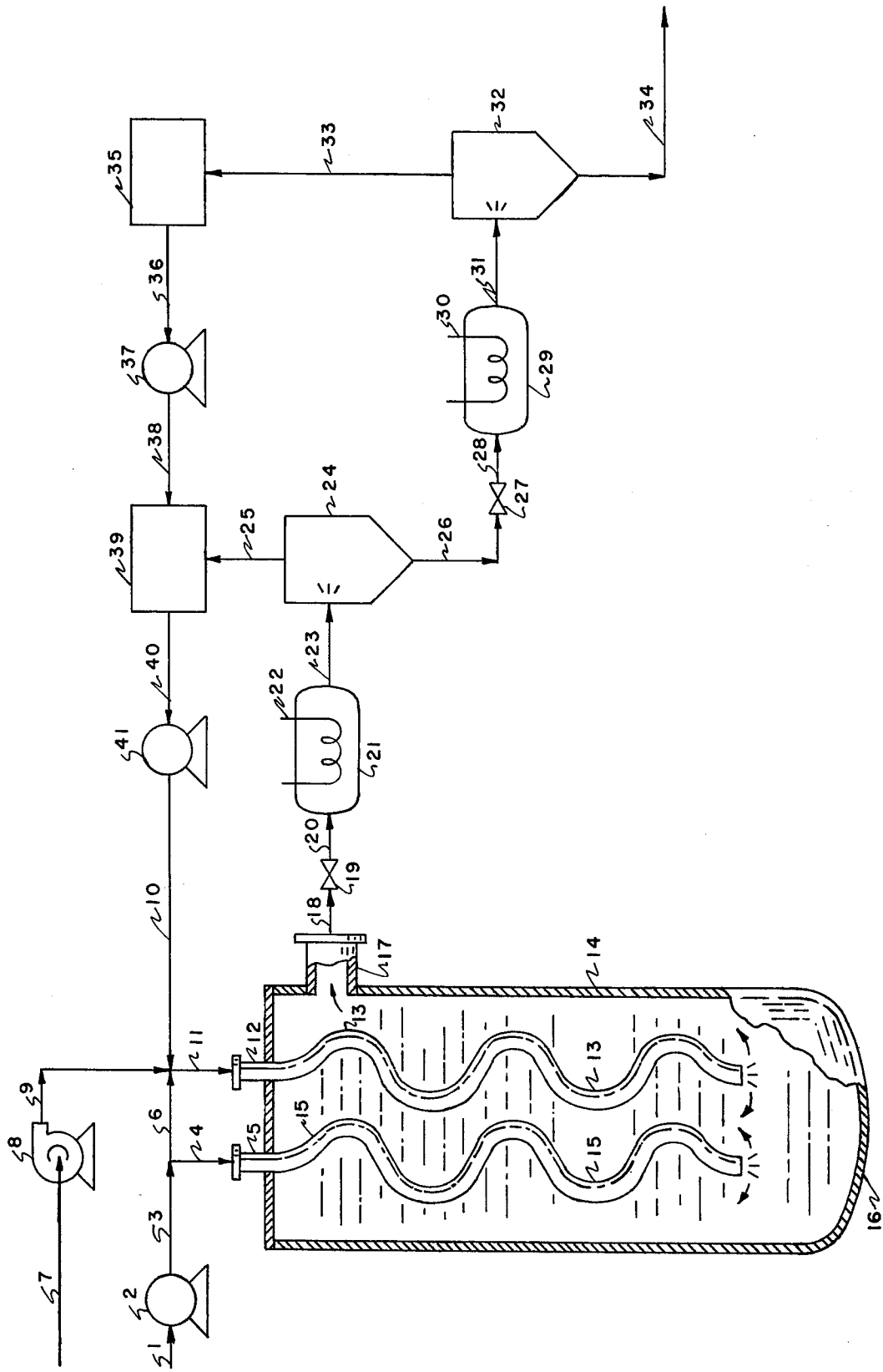

INTEGRATED TWO-STAGE UREA SYNTHESIS

BACKGROUND OF THE INVENTION

1. Field of the Invention

The invention relates to the high pressure synthesis of urea from ammonia and carbon dioxide via the intermediate formation of ammonium carbamate, and relates especially to the synthesis procedure.

2. Description of the Prior Art

Numerous arrangements of single or two stage urea synthesis reactors and procedures have been suggested in the prior art. Typical arrangements are disclosed in U.S. Pat. Nos. 3,270,051; 3,105,093 and 3,024,280; Canadian Pat. Nos. 1,160,030 and 1,147,734; French Pat. No. 958,503 and Belgian Pat. No. 522,822.

SUMMARY OF THE INVENTION

In the present invention, a procedure and apparatus for integrated two stage urea synthesis is provided. Feed streams of ammonia and carbon dioxide are combined with recycled aqueous ammonium carbamate solution to form a primary process stream having an overall ammonia to carbon dioxide molar ratio of about 2.5:1 and generally in the range of 2.3:1 to 30:1. This is close to the stoichiometric 2:1 ratio for the ammonium carbamate formation reaction, which rapidly takes place and liberates heat. The heat is employed for two purposes, to heat the subsequent intermediate process stream during ammonium carbamate dehydration to yield urea, and also to preheat an excess ammonia feed stream which is preheated by indirect heat exchange with the intermediate process stream. The heated excess ammonia stream is then added to the main process stream between stages, so as to form a combined intermediate reaction stream having an overall ammonia to carbon dioxide molar ratio of above 3.0:1 and generally in the range of 3.5:1 to 4.5:1. This combined stream then flows to the indirect heat exchanges and urea is formed. The resultant synthesis effluent stream is processed to form product aqueous urea solution and recycle aqueous ammonium carbamate solution.

The procedure of the present invention provides salient advantages in satisfying two stage reactor criteria which are prerequisites for more efficient urea synthesis, i.e. improvement in efficiency of the urea reactor by attaining a higher percentage conversion of carbon dioxide to urea and thereby reducing the consumption of steam, cooling water and power.

The first reactor criteria satisfied by the present invention is a feed mol ratio to the first stage of about 2.5 ammonia to 1 carbon dioxide. This includes the ammonia and carbon dioxide in the recycle carbamate solution. All of the makeup carbon dioxide and a part of the makeup ammonia are also fed to the first stage. The 2.5:1 ratio requires the lowest filling pressure at any temperature. The reaction mass is entirely in the liquid phase at the filling pressure. This means that all of the carbon dioxide will react with ammonia and go to molten ammonium carbamate. The required filling pressure rises rapidly at feed mol ratios above 2.5 ammonia/1 carbon dioxide, and also rises very rapidly as the ratio drops below 2.5:1. The nominal operating pressure of a conventional liquid recycle process is 3215 psia; feed mol ratio 4 ammonia/1 carbon dioxide; temperature 193°C. The filling pressure for this reaction mass is 3706 psia. In other words, the conventional liquid recycle process operates at 87% of filling pressure. The filling pressure for the 2.5:1 reaction mass is 3280 psia (vs. 3215 psia).

With regard to the second reactor criteria, the 4:1 conventional liquid recycle process reaction is in thermal balance since all of the heat of the ammonium carbamate reaction is used to preheat the reactants, the carbamate recycle solution; and, to supply the endothermic heat for the urea reaction. The heat from the first stage reaction in a two stage reactor is directly used to heat all of the reactants, except the differential quantity of excess ammonia, and the recycle carbamate solution. There is still an appreciable quantity of exothermic heat which must be conserved for the purpose of heating the differential quantity of excess ammonia, which is 1.5 mols in the case of a 4:1 reaction; and, supplying the heat for the urea reaction. The exothermic heat for the first stage reactor could be used to generate steam at a temperature somewhat below the temperature of the first stage reactor (less than 193°C); however, this steam cannot be used to supply the heat requirements of the second stage reaction if it is carried out in a separate reaction vessel operating at the same temperature. The ideal two stage reactor should therefore be one in which the two reaction stages are carried out in one reactor shell (integrated two stage reactor) so the exothermic heat from the first stage can be transferred indirectly to the second stage without the need for an intermediate heat carrier such as water, steam, oil or the like.

The third reactor criteria is that the feed streams to the integrated two stage reactor, i.e. feed streams to the first stage and the ammonia preheater, should pass down through separate heat transfer tubes; emerge and mix at the bottom of the integrated reactor shell; with the resulting mixture at about 4:1 molar ratio of ammonia to carbon dioxide rising up through the shell for the urea synthesis reaction. The first stage reactor should operate at a higher average temperature than the second stage or the ammonia preheater.

It is an object of the present invention to provide an improved process and apparatus for the synthesis of urea from ammonia and carbon dioxide.

Another object is to provide an improved urea synthesis reactor and procedure.

A further object is to utilize the exothermic heat of ammonium carbamate formation during urea synthesis in an improved manner.

An additional object is to provide an integrated two stage urea synthesis procedure and apparatus.

Still another object is to provide simultaneous ammonia preheating and heating of the urea synthesis process stream utilizing the heat of ammonium carbamate formation in an integrated reactor.

These and other objects and advantages of the present invention will become evident from the description which follows

DESCRIPTION OF THE DRAWING AND PREFERRED EMBODIMENTS

Referring now to the drawing, the urea synthesis reactor is shown in sectional elevation view, together with a typical flowsheet for the processing of the urea synthesis effluent stream discharged from the reactor. Liquid ammonia stream 1 is compressed by pump 2 to urea synthesis pressure, typically in the range of 2000 psig to 6000 psig, and the pressurized ammonia stream 3 discharged from unit 2 is divided into bypass stream 4 which passes to nozzles for preheating as will appear infra, and the main reactant stream 6.

Gaseous carbon dioxide feed stream 7 is compressed in compressor 8 to urea synthesis pressure, and the resulting compressed carbon dioxide gas stream 9 is combined with stream 6 and with recycled aqueous ammonium carbamate solution stream 10 to form the primary synthesis feed stream. The synthesis feed stream 11 is formed with an overall ammonia to carbon dioxide molar ratio generally in the range of 2.3:1 to 3.0:1 and preferably at substantially 2.5:1. This ratio is regulated by controlling the flow rate of stream 6, with the balance of stream 3 flowing as bypass excess ammonia stream 4.

Stream 11 now flows downwards via nozzle 12 into the preferably sinuous or serpentine primary reaction tube 13, which is preferably vertically disposed within the generally vertically oriented reaction container 14. Stream 11 flows downwards through tube 13 and further ammonium carbamate forms within tube 13 due to high pressure reaction of ammonia and carbon dioxide derived respectively from streams 6 and 9. The formation of ammonium carbamate within tube 13 is a highly exothermic reaction, and the heat liberated in the first reaction zone within tube 13 passes into the surrounding intermediate reaction mixture or stream within container 14. The hot main synthesis stream discharged into the lower end of container 14 from the lower end of tube 13 now consists primarily of molten ammonium carbamate, and may also contain a small proportion of urea, water and excess ammonia.

Ammonia stream 4 flows downwards via nozzle 5 into the preferably sinuous or serpentine ammonia preheat tube 15 which is preferably vertically disposed within the container 14. Stream 4 flows downwards through tube 15 and is preheated to optimum temperature by indirect heat exchange with the rising intermediate reaction stream within container 14. The preheated secondary ammonia is discharged from tube 15 at the lower end of container 14, so that a mixed process stream is formed by the combination of the streams discharged from tubes 13 and 15 adjacent to the lower end 16 of container 14. The mixed process stream or intermediate reaction stream is formed within container 14 adjacent to bottom 16 with an overall ammonia to carbon dioxide molar ratio generally above 3.0:1 and typically in the range of 3.5:1 to 4.5:1. A preferred molar ammonia to carbon dioxide ratio for this intermediate reaction stream at the lower end of container 14 is substantially 4:1.

The intermediate reaction stream rises within container 14 external to tubes 13 and 15, and heat is removed from tube 13 into the rising process stream, which also heats tube 15. As the intermediate reaction stream rises through container 14, retention time is provided for urea synthesis via ammonium carbamate dehydration.

A product urea synthesis effluent stream is removed from the upper end of container 14 via nozzle 17 as stream 18, which principally contains urea, residual ammonium carbamate, excess ammonia and water. Stream 18 is now subjected to any suitable processing for the recovery of product aqueous urea solution, and formation of aqueous ammonium carbamate solution for recycle via stream 10. Many suitable processing sequences for this purpose are known to those skilled in the art. Typical procedures are described in U.S. Pat. Nos. 3,527,799; 3,354,205; 3,270,050; 3,258,486; 3,191,916; 3,155,723; 3,155,722; 3,147,304; 3,137,725 and 3,091,637.

Stream 18 is thus typically processed in two stages, initially by passing stream 18 through pressure reducing valve 19. The resulting stream 20, now at a reduced pressure typically in the range of 200 psig to 400 psig, is heated in ammonium carbamate decomposer 21 by steam heating coil 22, which may alternatively consist of any suitable fluid heating device utilizing any suitable heating medium or process stream. The decomposition of ammonium carbamate in unit 21 generates a mixed gaseous phase containing ammonia, carbon dioxide and water vapor, and the resulting mixed gas-liquid stream 23 discharged from unit 21 is passed into gas-liquid separator 24, which is typically a baffled or cyclonic device for separation of gaseous and liquid phases. The mixed off-gas is removed from unit 24 via stream 25, which is processed to produce recycle aqueous ammonium carbamate solution as will appear infra.

The aqueous liquid phase removed from unit 24 via stream 26 now contains product urea as well as a minor residual proportion of ammonium carbamate. Stream 26 is passed through pressure reducing valve 27. The resulting stream 28, now at a further reduced pressure typically in the range of 15 psig to 50 psig, is heated in ammonium carbamate decomposer 29 by heating coil 30 which is usually a steam coil. The final decomposition of ammonium carbamate in unit 29 generates a gaseous phase containing ammonia, carbon dioxide and water vapor, and the resulting mixed gas-liquid stream 31 discharged from unit 29 is passed into gas-liquid separator 32, which is similar in configuration and function to unit 24 described supra. A mixed off-gas stream 33 is removed from unit 32, and product liquid consisting of aqueous urea solution is also removed from unit 32 via stream 34 which is passed to product finishing such as crystallization or prilling or the like, to produce product solid urea.

Stream 33 consisting of a mixed gaseous stream containing ammonia, carbon dioxide and water vapor is now subjected to partial or total condensation by cooling or the like, to condense an aqueous ammonium carbamate solution. Numerous types of arrangements or procedures may be provided to accomplish this result, and thus this generalized procedure will be understood to be accomplished by any of the diverse known procedures in unit 35. The condensed aqueous ammonium carbamate solution is withdrawn from unit 35 via stream 36, which is pressurized by pump 37 and passed as stream 38 to unit 39, which is generally similar in function to unit 35 and serves to condense further ammonium carbamate into the liquid phase from stream 25. The resultant concentrated aqueous ammonium carbamate solution formed in unit 39 flows via stream 40 to pump 41, which compresses the ammonium carbamate solution to urea synthesis pressure for recycle via stream 10.

Numerous alternatives within the scope of the present invention will occur to those skilled in the art. Reactor 14 and the tubes 13 and 15 may be of any suitable configuration and these elements may be horizontally oriented in suitable instances. The process streams flow may be upwards through the tubes 13 and 15 and downwards in container 14 to a lower outlet in suitable cases, and the tubes 13 and/or 15 may be straight linear tubes, or these tubes may be provided with external fins for improved heat transfer. It will be appreciated that stream 18 may be processed in any convenient fashion to produce product aqueous urea solution and aqueous ammonium carbamate solution for recycle. In this respect, units 35 and/or 39 may be operated to produce substantially pure gaseous ammonia as well as ammonium carbamate solution, as described in the patents cited supra. In this case, the excess ammonia recovered from units 35 and 39 will generally be recycled via stream 1. It will be understood that in most instances streams 36 and 40 will contain some proportion of dissolved excess ammonia, i.e. streams 36 and 40 will usually consist of aqueous ammoniacal ammonium carbamate solution.

An example of application of the present invention as compared to prior art one-stage conversion will now be described.

EXAMPLE

The reactor was operated at 3215 psig and 191°C. The overall feed mol proportions were 4 ammonia: 1 carbon dioxide: 0.58 water, with the molar ratio of ammonia to carbon dioxide of the combined stream 11 being 2.5:1 and 1.5 additional mols of ammonia being added via stream 4. Feed conditions were liquid ammonia at 130° F, carbon dioxide gas at 250° F and recycle ammonium carbamate solution at 200° F. Following is data relative to prior art one-stage conversion at 65% yield and overall two-stage conversion of carbon dioxide to urea at 70% and 72% yield, as well as a comparison of utility requirements.

Prior Art One Stage 65% Conversion, No Heat Recovery

Assume heat quantities as constants:

| Assume heat quantities as constants: | |
|---|---|
| Heat to desorb free ammonia: | 10,000 BTU/lb mol |
| Heat to decompose carbamate: | 63,000 BTU/lb mol |
| Heat to vaporize water: | 18,000 BTU/lb mol |
| Feed mol proportions: | |
| 4 ammonia/1 carbon dioxide/0.58 water | |

With all quantities specified as lb mols, the reactor effluent passed to the recovery system contained 2 free ammonia, 0.35 ammonium carbamate, 0.65 urea and 1.23 water. In addition, 0.11 water was added to the recovery system as liquid condensate. The product 74% aqueous urea solution discharged from the recovery system contained 0.65 urea and 0.76 water, or 1.17 mols water per mol urea. The recycle from the recovery system, which recycle was returned to urea synthesis, contained in the total quantity recycled as gas plus liquid, 2 free ammonia, 0.35 ammonium carbamate, and 0.58 water.

Heats were calculated as follows:

| | | |
|---|---|---|
| Free ammonia: | (2)(10000) | = 20,000 BTU |
| Ammonium carbamate: | (0.35)(63000) | = 22,000 BTU |
| Water: | (0.58−0.11)(18000) | = 8,450 BTU |
| | | 50,450 BTU |

| | | Total |
|---|---|---|
| Steam consumption, Tons/Ton Urea: | | |
| (50,450) / (0.65)(60)(1000) | = 1.3 T/T | |
| Cooling Water consumption Tons/Ton Urea at 20° F rise: | | |
| (50,450) / (0.65)(60)(20) | = 65 T/T | |

Present Process Two Stage 70% Conversion

| Total quantity recycled: | | |
|---|---|---|
| Free ammonia | 2 | |
| Ammonium carbamate | 0.30 | |
| Water | 0.58 | |
| Heats: Free ammonia | (2)(10,000) | = 20,000 BTU |
| Ammonium carbamate | (0.3)(63,000) | = 18,900 BTU |
| Water | (0.47)(18,000) | = 8,450 BTU |
| | | 47,350 BTU |

Steam consumption Tons/Ton Urea
(47,350) / (0.70)(60)(1000) = 1.13 T/T

Cooling Water consumption Tons/Ton Urea
(47,350) / (0.70)(60)(20) = 56.5 T/T

Present Process Two Stage 72% Conversion

| Heats: Free ammonia | (2)(10,000) | = 20,000 BTU |
|---|---|---|
| Ammonium carbamate | (0.28)(63,000) | = 17,600 BTU |
| Water | (0.47)(18,000) | = 8,450 BTU |
| | | 46,050 BTU Total |

Steam consumption:
(46,050) / (0.72)(60)(1000) = 1.07 T/T

Cooling water consumption:
(56,050)(2000) / (0.72)(60)(20)(2000) = 53 T/T

Following is a summary comparison of utility requirements.

STEAM AND COOLING WATER CONSUMPTION

| Number of Stages | % Conversion CO$_2$ to Urea | Prior Art Consumption, T/T | | Present Process with Heat Recovery, T/T | | |
|---|---|---|---|---|---|---|
| | | Steam | Cooling Water | Steam | Cooling Water 20° F Rise | 15° F Rise |
| 1 | 65 | 1.30 | 65 | 1.130 | 56.5 | 76 |
| 2 | 70 | 1.13 | 56.5 | 0.985 | 49.0 | 63 |
| 2 | 72 | 1.07 | 53 | 0.930 | 46 | 62 |

The decomposition load, mols ammonium carbamate per mol urea, may be summarized for the different conditions as follows:

| | One Stage | Two Stage | |
|---|---|---|---|
| % Conversion, Carbon Dioxide to Urea | 65 | 70 | 72 |
| Decomp. load, mols carb./mol Urea | 0.538 | 0.428 | 0.389 |

The utilities consumption is for production of 1 ton of urea as aqueous solution. Additional steam and/or cooling water would be required for finishing to solid urea.

It is evident that steam and cooling water consumption is reduced by 13% by practice of the invention, with 87% decomposition in the first stage.

I claim:

1. A process for urea synthesis which comprises combining carbon dioxide and primary ammonia feed streams with recycled aqueous ammonium carbamate solution to form a synthesis feed stream having an overall ammonia to carbon dioxide molar ratio in the range of 2.3:1 to 3.0:1, reacting said synthesis feed stream at elevated pressure to form further ammonium carbamate and generate heat in a first reaction zone and in indirect heat exchange with a urea synthesis reaction stream, heating secondary ammonia by indirect heat exchange with said urea synthesis reaction stream, adding the resulting heated secondary ammonia to the reacted synthesis feed stream principally containing ammonium carbamate, whereby said urea synthesis reaction stream is formed with a molar ammonia to carbon dioxide ratio above 3.0:1, reacting said urea synthesis reaction stream during said indirect heat exchanges with ammonia and synthesis feed stream in a second reaction zone, said second reaction zone being at substantially the same elevated pressure as said first reaction zone, whereby a major portion of the ammonium carbamate in said urea synthesis reaction stream is dehydrated to synthesize urea, and processing the resulting synthesis effluent stream at reduced pressure to recover aqueous urea solution and form said aqueous ammonium carbamate solution.

2. The process of claim 1, in which said urea synthesis reaction stream is formed with a molar ammonia to carbon dioxide ratio in the range of 3.5:1 to 4.5:1.

3. The process of claim 1, in which said first reaction zone is a tubular reactor within said second reaction zone.

4. The process of claim 1, in which said secondary ammonia is heated by indirect heat exchange with said urea synthesis reaction stream by passing said secondary ammonia through a tubular heater within said second reaction zone.

5. The process of claim 1, in which said resulting synthesis effluent stream is processed to recover aqueous urea solution and form said aqueous ammonium carbamate solution by heating said synthesis effluent stream at reduced pressure to decompose ammonium carbamate and form a mixed off-gas, separating said mixed off-gas from aqueous urea solution, and at least partially condensing said mixed off-gas to form said aqueous ammonium carbamate solution.

6. The process of claim 1, in which said synthesis feed stream flows downwards through a vertically oriented first reaction zone, said secondary ammonia is heated by passing said secondary ammonia downwards in indirect heat exchange with said second reaction zone, the resulting heated secondary ammonia and reacted synthesis feed stream are combined at the lower portion of said second reaction zone, and said second reaction zone is vertically oriented whereby said urea synthesis reaction stream flows upwards through said second reaction zone and said synthesis effluent stream is removed from the upper portion of said second reaction zone.

7. The process of claim 1, in which the molar ammonia to carbon dioxide ratio in said synthesis feed stream is substantially 2.5:1 and the molar ammonia to carbon dioxide ratio in said urea synthesis reaction stream is substantially 4:1.

* * * * *